(12) United States Patent
Daikoku et al.

(10) Patent No.: US 9,068,938 B2
(45) Date of Patent: Jun. 30, 2015

(54) TESTING METHOD USING GUIDED WAVE

(75) Inventors: Koki Daikoku, Kanagawa (JP); Masato Yoshizaki, Kanagawa (JP); Shuichi Sato, Kanagawa (JP)

(73) Assignee: IHI Inspection and Instrumentation Co., Ltd., Tokyo (JP)

( * ) Notice: Subject to any disclaimer, the term of this patent is extended or adjusted under 35 U.S.C. 154(b) by 326 days.

(21) Appl. No.: 13/574,187

(22) PCT Filed: Feb. 12, 2010

(86) PCT No.: PCT/JP2010/052070
§ 371 (c)(1),
(2), (4) Date: Jul. 19, 2012

(87) PCT Pub. No.: WO2011/089734
PCT Pub. Date: Jul. 28, 2011

(65) Prior Publication Data
US 2012/0291552 A1 Nov. 22, 2012

(30) Foreign Application Priority Data
Jan. 22, 2010 (JP) .................................. 2010-012278

(51) Int. Cl.
*G01N 9/24* (2006.01)
*G01N 29/44* (2006.01)
(Continued)

(52) U.S. Cl.
CPC ............ *G01N 29/44* (2013.01); *G01N 29/4472* (2013.01); *G01N 29/11* (2013.01);
(Continued)

(58) Field of Classification Search
CPC ................ G01N 2291/044; G01N 2291/2634; G01N 2291/048; G01N 29/265; G01N 29/11; G01N 29/07
USPC .................................... 73/599, 600, 622, 598
See application file for complete search history.

(56) References Cited

U.S. PATENT DOCUMENTS

| | | | |
|---|---|---|---|
| 4,825,423 A | 4/1989 | Yamanaka | |
| 7,234,355 B2 * | 6/2007 | Dewangan et al. | ............. 73/622 |

(Continued)

FOREIGN PATENT DOCUMENTS

| | | |
|---|---|---|
| JP | 61-76953 A | 4/1986 |
| JP | 5-75267 B2 | 10/1993 |

(Continued)

OTHER PUBLICATIONS

Office Action issued in co-pending related U.S. Appl. No. 13/574,151 on Jul. 24, 2014.
Toyokazu Komatsu et al., "Sensitivity of guided wave for gradually increasing defects to the axial direction of pipes", 2009 Nendo Nenji Taikai Koen Ronbunshu, vol. 9./No. 1, The Japan Society of Mechanical Engineers, Sep. 12, 2009, 451-452 (with partial translation).

(Continued)

*Primary Examiner* — Hezron E Williams
*Assistant Examiner* — Tarun Sinha
(74) *Attorney, Agent, or Firm* — Griffin & Szipl, P.C.

(57) ABSTRACT

(A) first data for defect amount estimation for the guided wave of a first frequency is obtained, the data indicating a relationship among amplitude of the reflected wave, a defect cross-sectional area and a defect width. (B) second data for defect amount estimation for the guided wave of a second frequency is obtained, the data indicating a relationship among amplitude of the reflected wave, a defect cross-sectional area and a defect width. (C) a guided wave of the first frequency is generated, and amplitude of a reflected wave is detected as first amplitude. (D) a guided wave of the second frequency is generated, and amplitude of a reflected wave is detected as second amplitude. (E) on a basis of the first and second data and the first and second amplitude, a defect cross-sectional area and a defect width of the defect part are estimated.

4 Claims, 5 Drawing Sheets

(51) Int. Cl.
*G01N 29/11* (2006.01)
*G01N 29/24* (2006.01)

(52) U.S. Cl.
CPC .... *G01N29/2412* (2013.01); *G01N 2291/0425* (2013.01); *G01N 2291/044* (2013.01); *G01N 2291/2634* (2013.01)

(56) References Cited

U.S. PATENT DOCUMENTS

| | | | |
|---|---|---|---|
| 7,634,392 B2 * | 12/2009 | Kwun et al. | 703/5 |
| 2004/0255678 A1 * | 12/2004 | Nagashima et al. | 73/620 |
| 2009/0031813 A1 | 2/2009 | Miki et al. | |

FOREIGN PATENT DOCUMENTS

| | | |
|---|---|---|
| JP | 8-30698 B2 | 3/1996 |
| JP | 2006-170754 A | 6/2006 |
| JP | 2008-292385 A | 12/2008 |
| JP | 2009-36516 A | 2/2009 |

OTHER PUBLICATIONS

Search Report issued in related application PCT/JP2010/052068, completed Mar. 3, 2010 and mailed Mar. 16, 2010.

Search Report issued in corresponding application PCT/JP2010/052070, completed Feb. 25, 2010 and mailed Mar. 9, 2010.

* cited by examiner

TESTING METHOD USING GUIDED WAVE

This is a National Phase Application in the United States of International Patent Application No. PCT/JP2010/052070 filed Feb. 12, 2010, which claims priority on Japanese Patent Application No. 012278/2010, filed Jan. 22, 2010. The entire disclosures of the above patent applications are hereby incorporated by reference.

TECHNICAL FIELD

The present invention relates to a testing method for a subject to be tested (hereinafter simply called a subject) in the shape of a tube or a rod. More particularly, the present invention relates to a testing method including the steps of: generating a guided wave that is a sound wave to propagate through a subject as a testing target in the longitudinal direction of the subject; detecting a reflected wave of the guided wave; and examining the subject on the basis of the reflected wave.

The guided wave typically has a frequency from 1 kHz to several hundreds kHz (in one example, 32 kHz, 64 kHz or 128 kHz).

BACKGROUND ART

A guided wave can be generated by the passage of AC current through a coil wound around a subject, for example. That is, AC current flowing through a coil wound around a subject generates AC magnetic field. A magnetic force from this AC magnetic field can be used to vibrate the subject, whereby a guided wave as a kind of sound waves can be generated. The thus-generated oscillation wave propagates through the subject along the longitudinal direction thereof.

A reflected wave of the guided wave is detected, whereby the soundness of the subject can be tested. A guided wave is reflected as a reflected wave at a discontinuous part of the subject or at a part of a change in cross-sectional area of the subject in the circumferential direction. This reflected wave is detected at an oscillation position of the guided wave, whereby the soundness of the subject is tested. The soundness of the subject is tested about the presence or absence of a defect part such as a flaw, corrosion or the like of the subject.

Examples of the guided wave include an L-mode (Longitudinal mode) guided wave and a T-mode (Torsional mode) guided wave. The L-mode guided wave propagates through a subject while vibrating in the propagation direction, and the T-mode guided wave propagates through a subject while torsionally vibrating in the subject.

Such a guided wave suffers less attenuation than a sound wave used for general sound wave testing, and therefore enables testing of a subject for the soundness over a wide range of the subject. A sound wave used for general sound wave testing has a high frequency of 5 MHz and a small wavelength of 0.6 mm, for example, and so is likely to attenuate. On the other hand, the above-stated guided wave has a small frequency of 32 kHz and a large wavelength of 100 mm, for example, and so suffers less attenuation.

The following Patent Document 1 is available, for example, as a prior art document of the present application.

PRIOR ART DOCUMENT

Patent Document

Patent Document 1: Japanese Patent Application Publication No. 2009-36516

SUMMARY OF THE INVENTION

Problem to be Solved by the Invention

Conventionally, a technique to locate the defect part is available. However, there is no technique of estimating the cross-sectional area and the width of the defect part at the same time. The position of a defect part can be obtained based on an elapsed time from oscillation timing of a guided wave to detection timing of a reflected wave thereof. On the other hand, conventionally there is no technique of estimating the cross-sectional area and the width of the defect part at the same time.

In view of this, it is an object of the present invention to provide a testing method using a guided wave capable of estimating the cross-sectional area and the width of a defect part of a subject at the same time.

Means for Solving the Problem

In order to fulfill such an object, a testing method using a guided wave of the present invention includes the steps of generating a guided wave to propagate through a subject in a shape of a rod or a tube as a testing target in a longitudinal direction of the subject, detecting a reflected wave of the guided wave and estimating a defect cross-sectional area and a defect width of a defect part existing in the subject on a basis of the reflected wave. The defect cross-sectional area refers to a cross-sectional area of the defect part taken along a plane orthogonal to an axial direction of the subject, and the defect width refers to a width of the defect part in the axial direction of the subject. In the method, (A) first data for defect amount estimation for the guided wave of a first frequency is obtained beforehand, the first data for defect amount estimation indicating a relationship among amplitude of the reflected wave, a defect cross-sectional area and a defect width, (B) second data for defect amount estimation for the guided wave of a second frequency is obtained beforehand, the second data for defect amount estimation indicating a relationship among amplitude of the reflected wave, a defect cross-sectional area and a defect width, (C) a guided wave of the first frequency is generated so as to propagate through the subject, and amplitude of a reflected wave of the guided wave is detected as first amplitude, (D) a guided wave of the second frequency is generated so as to propagate through the subject, and amplitude of a reflected wave of the guided wave is detected as second amplitude, and (E) on a basis of the first and second data for defect amount estimation and the first and second amplitude, a defect cross-sectional area and a defect width of the defect part are estimated.

According to a preferred embodiment of the present invention, the first data for defect amount estimation is represented by a following function F:

$$F(y,z)=x,$$

where x is a dependent variable and y, z are independent variables, and x denotes amplitude of the reflected wave, y denotes a defect cross-sectional area and z denotes a defect width, the second data for defect amount estimation is represented by a following function G:

$$G(y,z)=x,$$

where y, z are independent variables and x is a dependent variable, and x denotes amplitude of the reflected wave, y denotes a defect cross-sectional area and z denotes a defect width, and in (E), F(y, z)=$x_f$ and G(y, z)=$x_g$ are solved as a set of simultaneous equations, where $x_f$ denotes the first amplitude for the function F and $x_g$ denotes the second amplitude for the function G, whereby the defect cross-sectional area and the defect width of the defect part are calculated.

Preferably, in (A) or (B), (a) a subject for testing of a same type as the subject as a testing target is prepared; (b) a guided wave of the first or second frequency is propagated through the subject for testing and amplitude of a reflected wave thereof at a defect part is detected; (c) (b) is performed for a plurality of defect parts and, (d) on a basis of a defect cross-sectional area and a defect width of each of the plurality of defect parts in (c) and a plurality of the amplitude values obtained in (c), the first or second data for defect amount estimation is obtained.

Advantages of the Invention

According to the aforementioned present invention, data for defect amount estimation indicating a relationship among amplitude of a reflected wave, a defect cross-sectional area and a defect width is obtained beforehand for each of first and second frequencies, amplitude of a reflected wave reflected from a defect part of the subject as a testing target is detected for each of the first and second frequencies, and on the basis of each of data for defect amount estimation obtained beforehand and each detected amplitude value, a defect cross-sectional area and a defect width of the defect part are estimated.

Accordingly, the defect cross-sectional area and the defect width can be obtained at the same time.

EMBODIMENTS OF THE INVENTION

The following describes preferred embodiments of the present invention, with reference to the drawings. In the following drawings, the same reference numerals are assigned to common elements, and the duplicated description is omitted.

Figure 1:
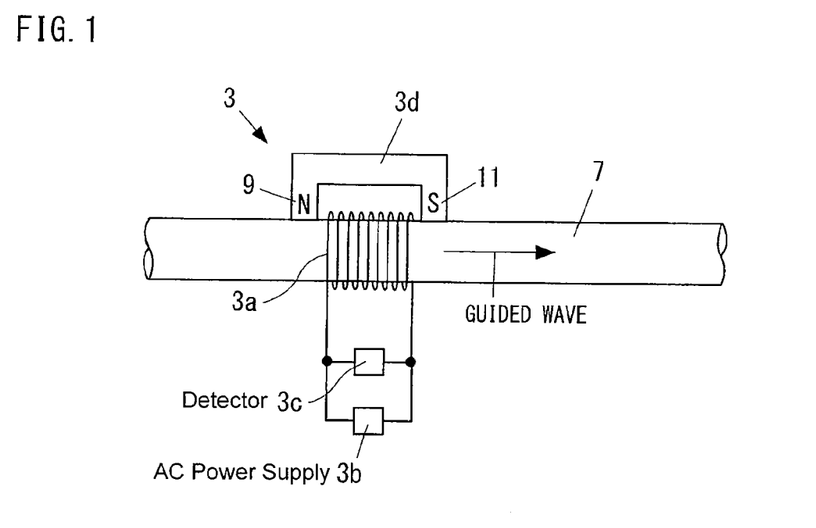
FIG. 1 illustrates an exemplary configuration of a testing device that can be used for a testing method using a guided wave according to an embodiment of the present invention.

FIG. 1 illustrates an exemplary configuration of a testing device 3 that can be used for a testing method using a guided wave according to an embodiment of the present invention. The testing device 3 of FIG. 1 is configured to generate an L-mode guided wave so as to propagate through a subject 7 as a testing target made of metal, glass, resin or the like in the longitudinal direction, detect a reflected wave of the guided wave and examine the subject 7 based on the reflected wave.

The testing device 3 includes a coil 3a, a magnet 3d, an AC power supply 3b and a detector 3c.

The subject 7 is tubular or a rod-shaped. For instance, the tubular subject 7 may be piping through which fluid flows, and the rod-shaped subject 7 may be a ground anchor, an anchor bolt or a reinforcing iron bar.

The coil 3a is wound around the subject 7. The magnet 3d is disposed so that the north pole 9 thereof is located on one side of the coil 3a in the axial direction of the subject 7, and the south pole 11 thereof is located on the other side of the coil 3a, and the coil 3a is sandwiched between the north pole 9 and the south pole 11. These north pole 9 and south pole 11 are fixed to an outer periphery face of the subject 7 with appropriate means such that these poles are pressed toward the center axis of the subject 7. The detector 3c is connected to the coil 3a for detection of a voltage between both ends of the coil 3a.

Arranging the coil 3a, the magnet 3d and the detector 3c in this way, when AC current is passed through the coil 3a from the AC power supply 3b, an L-mode guided wave is generated in the subject 7, and the guided wave propagates along the longitudinal direction of the subject 7. Such a propagating guided wave is reflected at a defect part such as a flaw or corrosion (wastage) of the subject 7 and returns to the coil 3a side by propagation. The detector 3c detects a voltage generated between both ends of the coil 3a as the reflected wave reaches the part of the subject 7 around which the coil 3a is wound.

Figure 2:
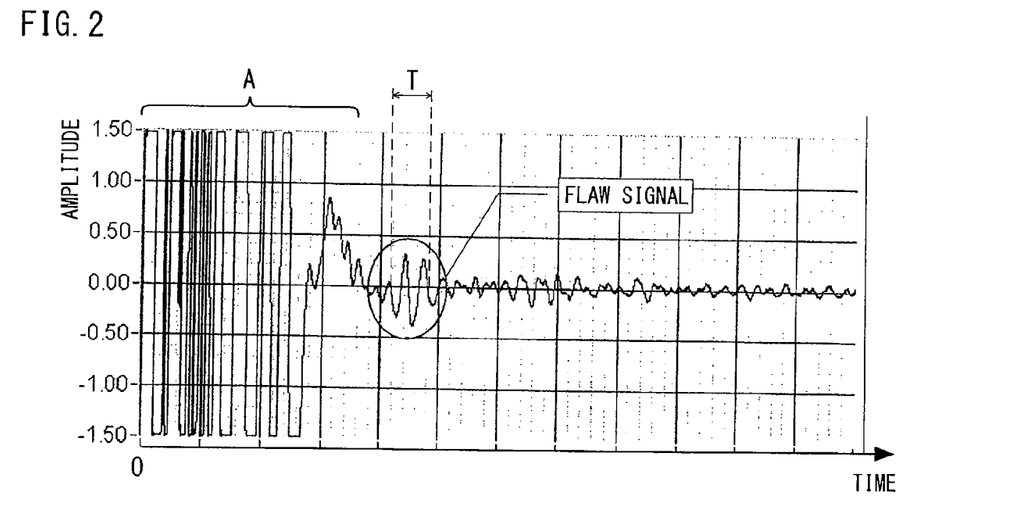
FIG. 2 illustrates a waveform of a reflected wave that the testing device of FIG. 1 actually detected.

FIG. 2 illustrates a waveform of the reflected wave that the detector 3c of the testing device 3 of FIG. 1 actually detected. In FIG. 2, the horizontal axis represents time (corresponding to a distance from the attachment position of the coil 3a along the longitudinal direction of the subject 7). The vertical axis represents amplitude of a voltage (i.e., amplitude of the reflected wave) between both ends of the coil 3a. In FIG. 2, the waveform shows that the amplitude of the reflected wave is larger at the part surrounded with the circle (flaw signal) than at other parts, meaning that there is a defect such as a flaw or corrosion at a position of the subject 7 corresponding to this surrounded part. In FIG. 2, the waveform in the range A shows a voltage applied from AC power supply 3b at the time of the generation of the guided wave. The origin of the time in FIG. 2 corresponds to the time when the guided wave is generated.

Figure 3:
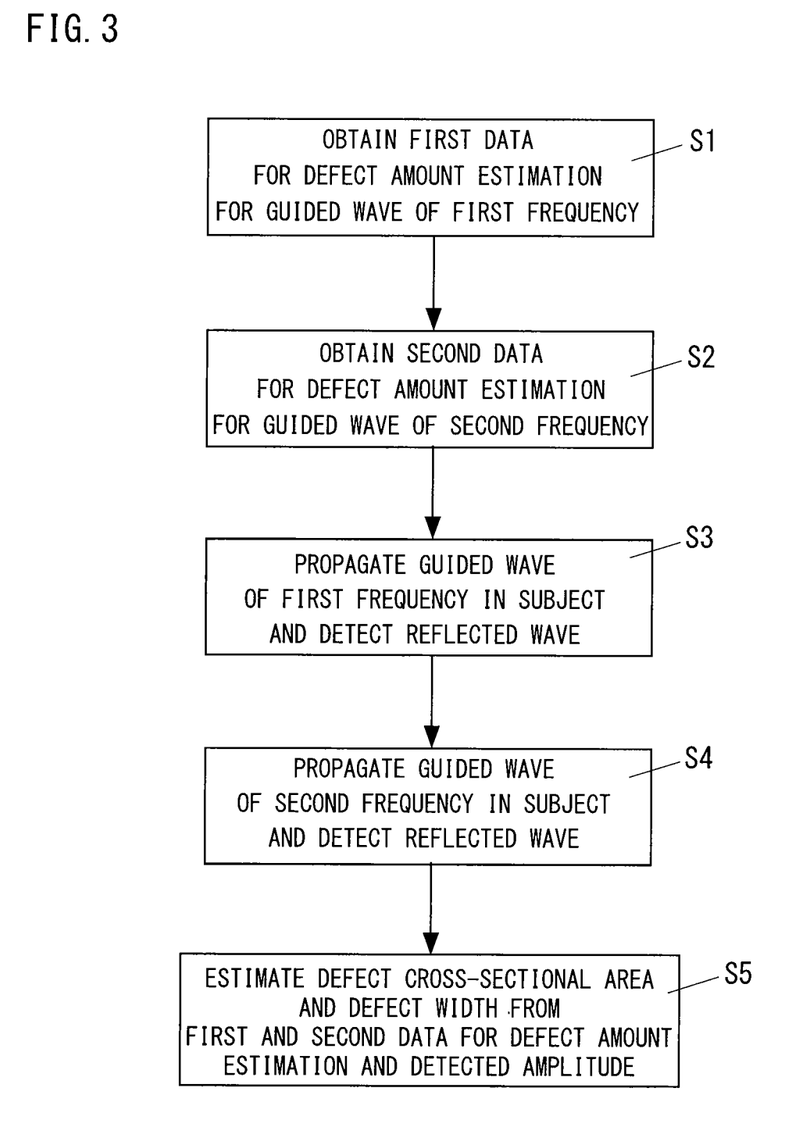
FIG. 3 is a flowchart showing a testing method using a guided wave according to an embodiment of the present invention.

FIG. 3 is a flowchart showing a testing method using a guided wave according to an embodiment of the present invention. This testing method includes the steps of: generating a guided wave to propagate through a subject 7 as a testing target in the shape of a rod or a tube in the longitudinal direction of the subject; detecting a reflected wave of the guided wave; and estimating a defect cross-sectional area and a defect width of a defect part existing in the subject 7 on a basis of the reflected wave. In the present application, the defect cross-sectional area refers to a cross-sectional area of a defect part taken along a plane orthogonal to an axial direction of the subject 7 (or a subject 8 described later), and the defect width refers to a width of a defect part in the axial direction of the subject 7 (or a subject 8 described later).

At Step S1, first data for defect amount estimation is obtained beforehand, the first data for defect amount estimation indicating a relationship among amplitude of a reflected wave of a guided wave of a first frequency (e.g., 16 kHz), a defect cross-sectional area and a defect width.

Preferably at Step S1, the following (a) to (d) are performed: (a) a subject 8 for testing of the same type as the subject 7 as a testing target is prepared; (b) a guided wave of the first frequency is propagated through the subject 8 for testing and amplitude of a reflected wave thereof at a defect part is detected by the testing device 3; (c) (b) is performed for a plurality of defect parts; and (d) on the basis of a defect cross-sectional area and a defect width of each of the plurality of defect parts in (c) and a plurality of the amplitude values obtained in (c), the first data for defect amount estimation is obtained.

The first data for defect amount estimation is represented by the following function F:

$$F(y,z)=x,$$

where x is a dependent variable and y, z are independent variables, and x denotes amplitude of the reflected wave, y denotes a defect cross-sectional area and z denotes a defect width.

Figure 4A:
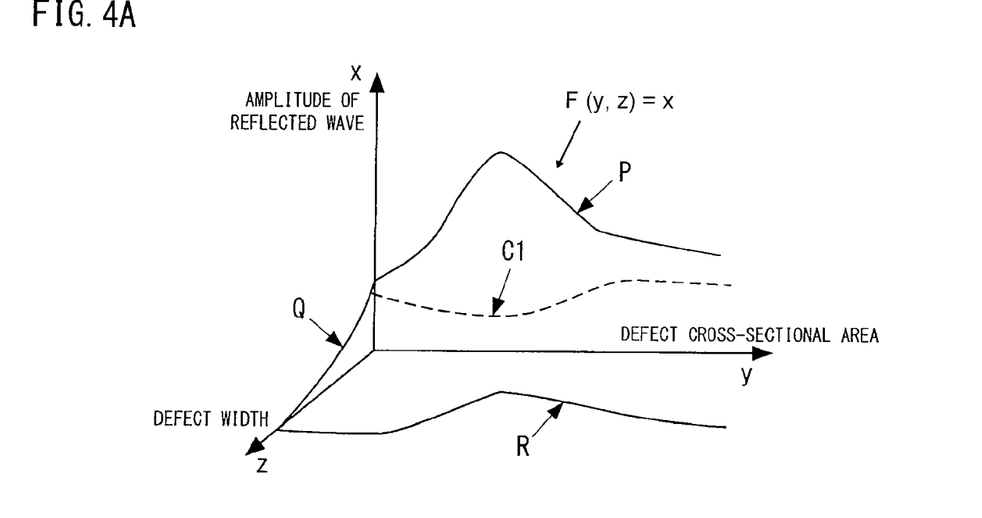
FIG. 4A shows first data for defect amount estimation.

As illustrated in FIG. 4A as one example, the first data for defect amount estimation (i.e., the above function F) can be represented with a curved face in a three-dimensional coordinate space, and the three-dimensional coordinate space has mutually intersecting axes including a coordinate axis x representing the amplitude of a reflected wave of a guided wave of the first frequency, a coordinate axis y representing a defect cross-sectional area and a coordinate axis z representing a defect width. In FIG. 4A, a curve part P indicated with a solid line is a part where the curved face as the first data for defect amount estimation interests the x-y plane. In FIG. 4A, a curve part Q indicated with a solid line is a part where the curved face as the first data for defect amount estimation interests the x-z plane. In FIG. 4A, a curve part R indicated with a solid line is a part where the curved face as the first data for defect amount estimation interests the y-z plane.

At Step S2, second data for defect amount estimation is obtained beforehand, the second data for defect amount estimation indicating a relationship among amplitude of a reflected wave of a guided wave of a second frequency (e.g., 32 kHz), a defect cross-sectional area and a defect width.

Preferably at Step S2, the following (a) to (d) are performed: (a) a subject 8 for testing of the same type as the subject 7 as a testing target is prepared; (b) a guided wave of the second frequency is propagated through the subject 8 for testing and amplitude of a reflected wave thereof at a defect part is detected by the testing device 3; (c) (b) is performed for a plurality of defect parts; and (d) on the basis of a defect cross-sectional area and a defect width of each of the plurality of defect parts in (c) and a plurality of the amplitude values obtained in (c), the second data for defect amount estimation is obtained.

The second data for defect amount estimation is represented by the following function G:

$$G(y,z)=x,$$

where x is a dependent variable and y, z are independent variables, and x denotes amplitude of the reflected wave, y denotes a defect cross-sectional area and z denotes a defect width.

Figure 4B:
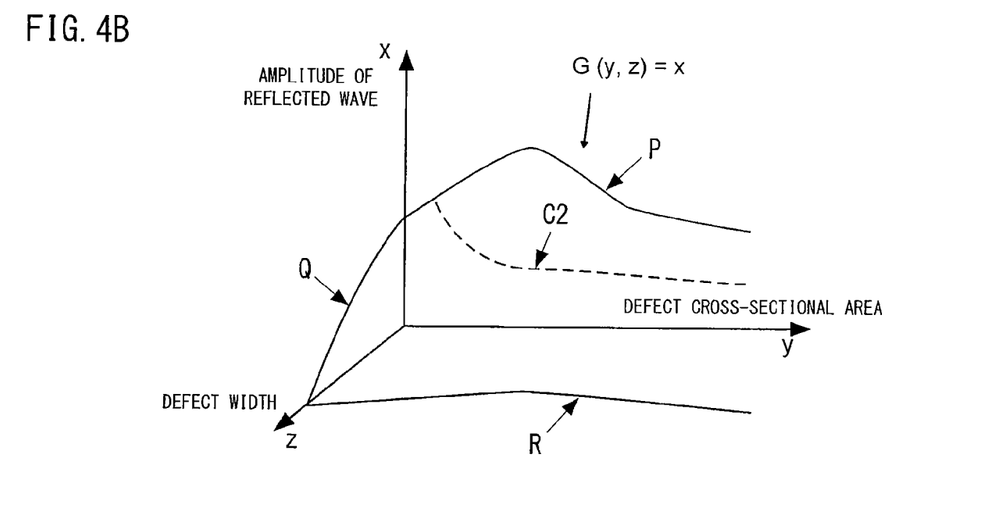
FIG. 4B shows second data for defect amount estimation.

As illustrated in FIG. 4B as one example, the second data for defect amount estimation (i.e., the above function G) can be represented with a curved face in a three-dimensional coordinate space, and the three-dimensional coordinate space includes mutually intersecting axes including a coordinate axis x representing the amplitude of a reflected wave of a guided wave of the second frequency, a coordinate axis y representing a defect cross-sectional area and a coordinate axis z representing a defect width. In FIG. 4B, a curve part P indicated with a solid line is a part where the curved face as the second data for defect amount estimation interests the x-y plane. In FIG. 4B, a curve part Q indicated with a solid line is a part where the curved face as the second data for defect amount estimation interests the x-z plane. In FIG. 4B, a curve part R indicated with a solid line is a part where the curved face as the second data for defect amount estimation interests the y-z plane.

At Step S3, a guided wave of the first frequency to propagate through the subject 7 is generated, and amplitude of a reflected wave of this guided wave is detected as first amplitude. More specifically, this step is as follows. Firstly, the testing device 3 is attached at an attachment position of the subject 7 as a testing target. That is, at the attachment position located at a predetermined part in the axial direction of the subject 7, the coil 3a is wound around an outer periphery face of the subject 7 about an axis of the subject 7. Then the magnet 3d, the AC power supply 3b and the testing device 3 are arranged as stated above. Next, a switch provided at a wiring connecting the AC power supply 3b and the coil 3a is turned on with appropriate means, whereby AC current of the first frequency is passed through the coil 3a. As a result an L-mode guided wave of the first frequency is generated, and this guided wave propagates along the longitudinal direction of the subject 7 as a testing target. A reflected wave of such an L-mode guided wave propagating through the subject 7 is detected by the detector 3c. The detector 3c acquires the waveform of the reflected wave as illustrated in FIG. 2, for example.

Preferably, the testing device 3 used at Step S3 is the same as the testing device 3 used at Step S1.

Preferably, the magnitude (amplitude) of the AC current passed through the coil 3a at Step S3 is the same as the magnitude (amplitude) of the AC current passed through the coil 3a at Step S1.

At Step S4, a guided wave of the second frequency to propagate through the subject 7 is generated, and amplitude of a reflected wave of this guided wave is detected as second amplitude. More specifically, this step is as follows. Firstly, the testing device 3 is attached at an attachment position of the subject 7 as a testing target. That is, at the attachment position located at a predetermined part in the axial direction of the subject 7, the coil 3a is wound around an outer periphery face of the subject 7 about a core of the subject 7. Then the magnet 3d, the AC power supply 3b and the testing device 3 are arranged as stated above. Next, a switch provided at a wiring connecting the AC power supply 3b and the coil 3a is turned on with appropriate means, whereby AC current of the second frequency is passed through the coil 3a. As a result an L-mode guided wave of the second frequency is generated, and this guided wave propagates along the longitudinal direction of the subject 7 as a testing target. A reflected wave of such an L-mode guided wave propagating through the subject 7 is detected by the detector 3c.

Preferably, the testing device 3 used at Step S4 is the same as the testing device 3 used at Step S2. Preferably, the magnitude (amplitude) of the AC current passed through the coil 3a at Step S4 is the same as the magnitude (amplitude) of the AC current passed through the coil 3a at Step S2.

At Step S5, on the basis of the first and second data for defect amount estimation and the first and second amplitude, a defect cross-sectional area and a defect width of the defect part are estimated.

Preferably, at Step S5, $F(y, z)=x_f$ and $G(y, z)=x_g$ are solved as a set of simultaneous equations, where $x_f$ denotes the first amplitude for the function F and $x_g$ denotes the second amplitude for the function G, whereby the defect cross-sectional area y and the defect width z of the defect part are calculated.

Figure 4C:
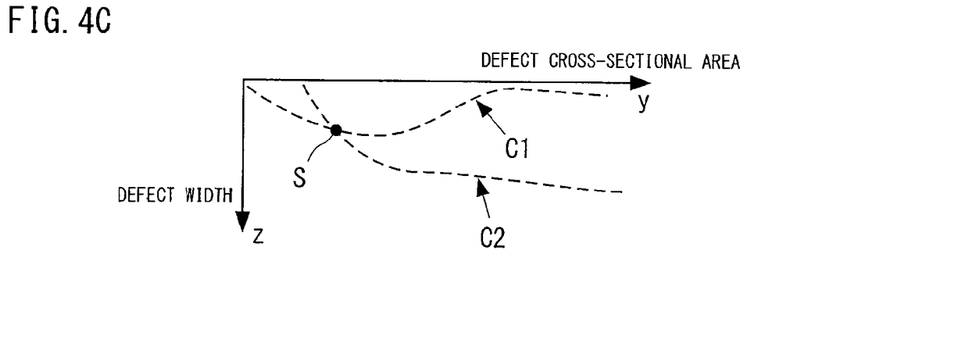
FIG. 4C shows a position S corresponding to a defect cross-sectional area and a defect width to be found.

Referring to FIG. 4A to FIG. 4C, Step S5 is described below. To solve the functions F and B as a set of simultaneous equations means the followings.

At Step S5, in the curved face as the first data for defect amount estimation (i.e., the curved face representing the function F), a part corresponding to the first amplitude $x_f$ (e.g., a broken-lines part C1 of FIG. 4A) is extracted as a first curve, and in the curved face as the second data for defect amount estimation (i.e., the curved face representing the function G), a part corresponding to the second amplitude $x_g$ (e.g., a broken-lines part C2 of FIG. 4B) is extracted as a second curve. Then, on the basis of the first and second curves C1 and C2, the defect cross-sectional area and the defect width of the defect part are estimated. For instance, as illustrated in FIG. 4C, in a two-dimensional coordinate space (two-dimensional plane) having mutually intersecting axes including a coordinate axis y representing a defect cross-sectional area and a coordinate axis z representing a defect width, the first and second curves C1 and C2 are projected in the x-axial direction, and in the two-dimensional coordinate space, an intersection S where the projected first and second curves C1 and C2 intersect is found, and a defect cross-sectional area and a defect width corresponding to the intersection S are estimated as the defect cross-sectional area and the defect width of the defect part. Herein, preferably at Steps S1 to S4, the time duration for which the switch is being turned on is controlled so that a guided wave of a desired short length (e.g., about two to three wavelengths) is generated for propagation. After such time duration for which the switch is being turned on, then the switch is turned off so as not to pass current from the AC power supply 3b to the coil 3a.

(Defect Cross-Sectional Area and Defect Width)

Figure 5A:
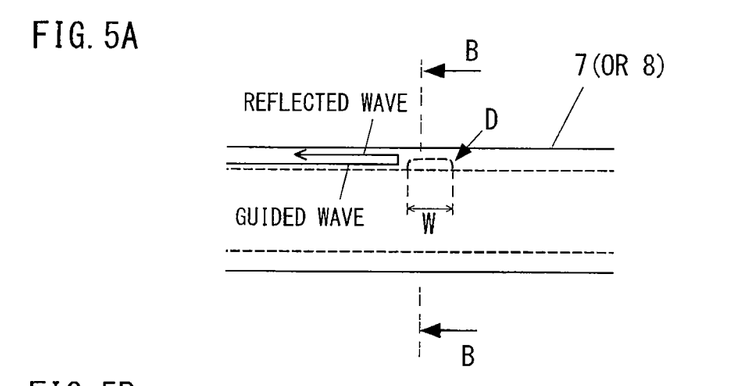
FIG. 5A illustrates a defect width of a defect part D.
Figure 5B:
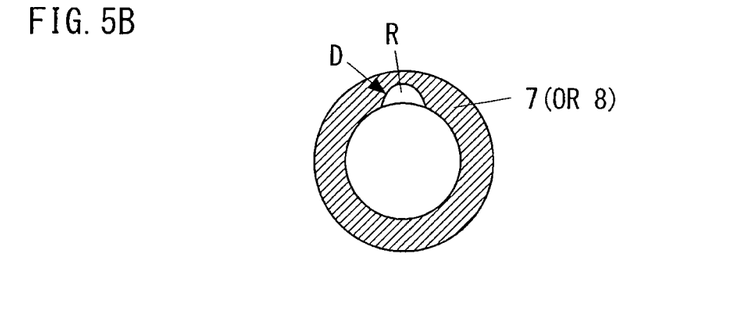
FIG. 5B illustrates a defect cross-sectional area of a defect part D.

FIG. 5A and FIG. 5B show a defect width and a defect cross-sectional area of a defect part D. FIG. 5B is a cross-sectional view taken along the line B-B of FIG. 5A, and illustrates a cross section of the subject 7 or 8. The region R in FIG. 5B indicates a cross-sectional area of the defect part D. In FIG. 5A, W denotes the width of the defect part D of the subject 7 or 8.

The procedure to obtain the first data for defect amount estimation at Step S1 is described below in more detail.

Figure 6:
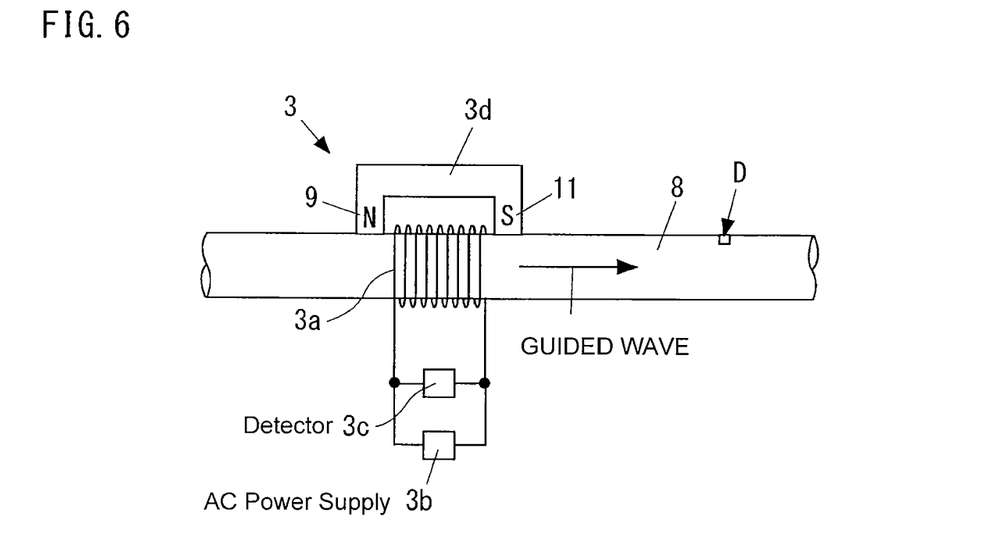
FIG. 6 illustrates the testing device of FIG. 1 attached to a subject as a testing target.

Firstly, a subject 8 for testing of the same type (i.e., the same material, dimensions and shape) as the subject 7 as a testing target is prepared, and the testing device 3 is attached to this subject 8 for testing as illustrated in FIG. 6. The way of attaching the testing device 3 is the same as the above-described way. A part of the subject 8 is cut away using an appropriate tool from the outer periphery face side, whereby a first defect part D is formed at the outer periphery face of the subject 8 as illustrated in FIG. 6.

Next, a guided wave at the same first frequency and the same amplitude as the guided wave to be generated at Step S3 is generated by the testing device 3 attached to the subject 8 so that the guide propagates through the subject 8. A reflected wave of the guided wave reflected from the first defect part D is detected. Such a reflected wave is displayed, as a waveform part like the flaw signal of FIG. 2, on a display of the detector 3c configured to display the waveform as in FIG. 2. The amplitude (preferably the maximum value of the amplitude) of the reflected wave is recorded and stored in the detector 3c.

Next, a new defect part D having at least one of a cross-sectional area and a width different from those of the first defect part D is formed in the same manner as in the above. Herein, the subject 8 may be further cut away at the first defect part D to form the new defect part D having a larger cross-sectional area. Following the formation of such a new defect part D, in the same manner as in the above, a guided wave having the same first frequency and the same amplitude as those of the guided wave to be generated at Step S3 is generated, the guided wave is propagated through the subject 8, a reflected wave of the guided wave reflected from the new defect part D is detected, and the amplitude thereof (preferably the maximum value of the amplitude) is recorded.

Thereafter still another defect part having at least one of a different cross-sectional area and a different width is formed in the same manner as in the above, a guided wave having the same first frequency and the same amplitude as those of the guided wave to be generated at Step S3 is generated in the same manner as in the above, the guide is propagated through the subject 8, a reflected wave of a guided wave reflected from the defect part D is detected, and the amplitude thereof (preferably the maximum value of the amplitude) is recorded.

Such procedure is repeated, whereby data containing the defect cross-sectional area values and the defect width values (known) of the plurality of (preferably a large number of) defect parts D and a plurality of amplitude values of the reflected waves corresponding to these plurality of (preferably a large number of) defect cross-sectional area values and defect width values is acquired. Based on this data, the first data for defect amount estimation is obtained.

At Step S2, the procedure to obtain the second data for defect amount estimation is the same as the procedure to obtain the first data for defect amount estimation expect for that the frequency of the guided wave used is the second frequency.

FIG. 6 illustrates the tubular subject 8. In the case of a rod-shaped subject 8, however, a defect part may be formed at an outer periphery part of the subject 8. In this case, a defect amount due to corrosion or the like can be estimated for a subject 7 that is embedded in the ground or a structure.

Preferably, attenuation of a reflected wave is considered. More specifically, a subject for attenuation testing of the same type (i.e., the same material, dimensions and shape) as the subject 7 as a testing target is prepared. Next, defect parts are formed at a plurality of positions in the axial direction of the subject for attenuation testing to have the same cross-sectional area (i.e., cross-sectional area taken along a plane orthogonal to the axial direction of the subject for attenuation testing) and the same width (i.e., width in the axial direction of the subject for attenuation testing). Thereafter, a guided wave is generated for propagation through the subject for attenuation testing using the aforementioned testing device 3, reflected waves from the respective defect parts are detected, and on the basis of the amplitude values of the reflected waves and the positions of the defect parts in the axial direction, and a relationship (called an attenuation relationship) between a distance from the attachment position of the coil 3a to the reflecting position of the guided waves (i.e., corresponding to the positions of the defect parts in the axial direction) and an attenuation amount or an attenuation ratio (attenuation ratio of the reflected wave with reference to the distance) of the amplitude of the reflected wave is obtained.

In this case, on the basis of the attenuation relationship, the first and second data for defect amount estimation obtained at Steps S1 and S2, the first and second amplitude detected at Steps S3 and S4, a defect cross-sectional area and a defect width of the defect part of the subject 7 as a testing target is estimated with consideration given to the attenuation of the reflected wave. For instance, the amplitude of the reflected waves detected at Steps S3 and S4 is corrected to the amplitude to be free from the attenuation on the basis of the reflecting position of the reflected wave and the attenuation relationship, and this corrected first and second amplitude is applied to the first and second data for defect amount estimation, whereby a defect cross-sectional area and a defect width of the subject 7 may be estimated. In this case, for example, at each of Steps S1 and S2, as for a plurality of defect parts, on the basis of the position of the defect parts, the position of the coil 3a, the amplitude of the reflected wave and the attenuation relationship, the data for defect amount estimation without attenuation in reflected wave is obtained.

The first and second data for defect amount estimation may be stored in the aforementioned detector 3c. Then, the detector 3c may recognize the first and second amplitude of the reflected wave, and may estimate values of the defect cross-sectional area and the defect width at Step S5 on the basis of the first and second amplitude and the first and second data for defect amount estimation.

According to the aforementioned embodiment of the present invention, data for defect amount estimation is obtained beforehand for each of first and second frequencies, the data for defect amount estimation indicating a relationship among amplitude of a reflected wave, a defect cross-sectional area and a defect width, amplitude of a reflected wave reflected from a defect part of the subject 7 as a testing target is detected for each of the first and second frequencies, and on the basis of each of data for defect amount estimation obtained beforehand and each detected amplitude value, a defect cross-sectional area and a defect width of the defect part are estimated. Accordingly, the defect cross-sectional area and the defect width can be obtained at the same time.

The present invention is not limited to the aforementioned embodiments and can be variously modified without departing from the scope of the present invention.

For instance, when the subject has a rod shape, a defect part will be located mainly on an outer periphery face of the subject. On the other hand, when the subject has a tubular shape, a defect part may be on an inner periphery face or on an outer periphery face of the subject. Accordingly, in order to obtain the data for defect amount estimation, a defect part may be formed on the outer periphery surface or on the inner periphery surface of the subject 8 for testing. In the aforementioned embodiment, the subject 8 is cut away from the outer periphery face side, whereby a plurality of defect parts are formed on the outer periphery face of the subject 8 for testing, and the data for defect amount estimation is obtained on the basis of reflected waves from these defect parts. The thus-obtained data for defect amount estimation is applicable precisely to the case of estimating a defect cross-sectional area and a defect width of a defect part on the inner periphery face of the subject 7 as a testing target as well. That is, the data for defect amount estimation obtained using defect parts formed on the outer periphery face of the subject 8 for testing is almost equal to the data for defect amount estimation obtained using defect parts formed on the inner periphery face of the subject 8 for testing. Accordingly, the data for defect amount estimation may be obtained using defect parts formed on the outer periphery face of the subject 8 for testing or using defect parts formed on the inner periphery face of the subject 8 for testing. Herein, defect parts can be more easily formed on the outer periphery face.

Figure 7:
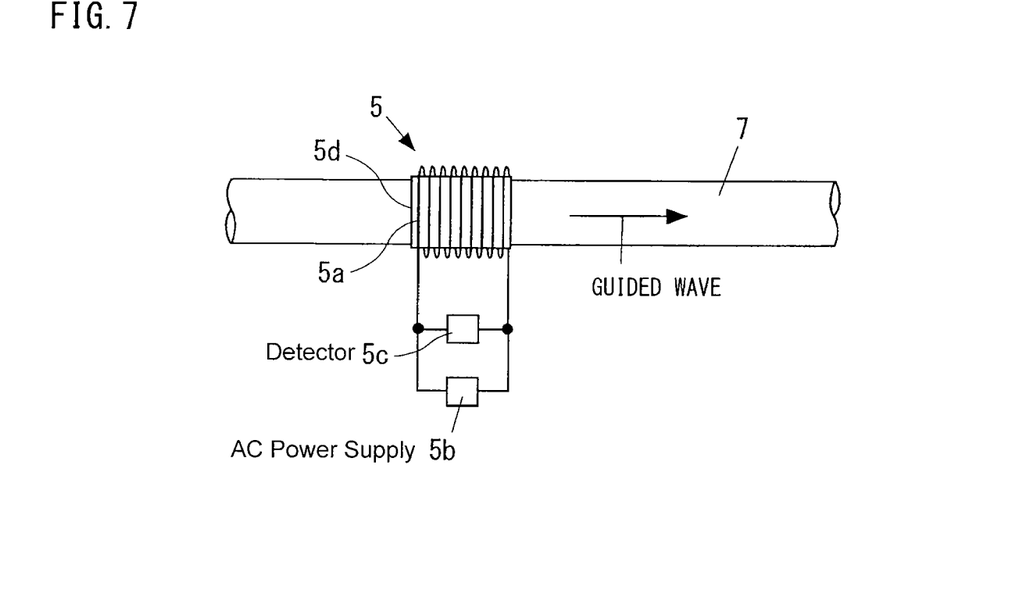
FIG. 7 illustrates another exemplary configuration of a testing device that can be used for a testing method using a guided wave according to the present invention.

Although the aforementioned embodiments use the testing device 3 using an L-mode guided wave, a testing device using another mode may be used. For instance, the aforementioned Step S3 or S4 may be performed using a testing device 5 using a T-mode guided wave as illustrated in FIG. 7. In this case, the mode of the guided wave used in the aforementioned Step S3 may be different from that of the guided wave used in the aforementioned Step S4.

The testing device 5 of FIG. 7 includes a ferromagnetic metal plate 5d, a coil 5a, an AC power supply 5b and a detector 5c. The ferromagnetic metal plate 5d is a metal plate made of a ferromagnetic material, and the ferromagnetic metal plate 5d is directly wound around an outer periphery face of the subject 7. The coil 5a is wound on the ferromagnetic metal plate 5d around the subject 7. The detector 5c is connected to the coil 5a for detection of a voltage between both ends of the coil 5a. Attaching the ferromagnetic metal plate 5d, the coil 5a and the detector 5c in this way, when AC current is passed through the coil 5a from the AC power supply 5b, a T-mode guided wave is generated in the subject 7, and the guided wave propagates along the longitudinal direction of the subject 7. Such a propagating guided wave is reflected at a defect part such as a flaw or corrosion (wastage) of the subject 7 and returns to the coil 5a side by propagation. The detector 5c detects a voltage generated between both ends of the coil 5a as the reflected wave reaches the part of the coil 5a.

The configuration of the testing device 3, 5 is not limited to the exemplary configurations illustrated in FIG. 1 and FIG. 7.

At Step S1 or S2, a plurality of defect parts D having different defect cross-sectional areas and defect widths are formed in the subject 8 for testing at different known positions in the axial direction. In this state, a guided wave is generated by a testing device attached to the subject 8 at a known position, reflected waves from the defect parts D are detected, the amplitude values of these reflected waves are corrected to amplitude values without attenuation on the basis of the attenuation relationship, and on the basis of the thus-corrected amplitude values and the plurality of known cross-sectional areas and widths, the data for defect amount estimation may be obtained.

Although not illustrated and described, the testing device may be provided with a cancellation device configured to intensify the amplitude of the guided wave propagating in one of two opposed axial directions of the subject and cancel the guided wave in the other axial direction. Similarly to the testing devices, such a cancellation device includes a coil and an AC power supply, and the coil is wound around the subject at a position away from the coil of the testing device by ¼ of the wavelength of the guided wave, and the coil of the cancellation device generates a guided wave out of phase by ¼ of the cycle of the guided wave generated by the coil of the testing device. Such a cancellation device allows a guided wave to propagate in one axial direction only.

DESCRIPTION OF REFERENCE NUMERALS

3: Testing device, 3a: Coil, 3b: AC power supply 3c: Detector, 3d: Magnet, 5: Testing device 5a: Coil, 5b: AC power supply, 5c: Detector 5d: Ferromagnetic metal plate, 7: Subject as testing target 8: Subject for testing, 9: North pole, 11: South pole

The invention claimed is:

1. A testing method using a guided wave, of generating a guided wave to propagate through a subject in a shape of a rod or a tube as a testing target in a longitudinal direction of the subject, detecting a reflected wave of the guided wave and estimating a defect cross-sectional area and a defect width of a defect part existing in the subject on a basis of the reflected wave, wherein the defect cross-sectional area refers to a cross-sectional area of the defect part taken along a plane orthogonal to an axial direction of the subject, and the defect width refers to a width of the defect part in the axial direction of the subject, wherein the method comprises the steps of:

(A) obtaining first data for defect amount estimation for the guided wave of a first frequency beforehand, the first data for defect amount estimation indicating a relationship among amplitude of the reflected wave, a defect cross-sectional area and a defect width, (B) obtaining second data for defect amount estimation for the guided wave of a second frequency beforehand, the second data for defect amount estimation indicating a relationship among amplitude of the reflected wave, a defect cross-sectional area and a defect width, (C) generating a guided wave of the first frequency so as to propagate through the subject, and detecting amplitude of a reflected wave of the guided wave as first amplitude, (D) generating a guided wave of the second frequency so as to propagate through the subject, and detecting amplitude of a reflected wave of the guided wave as second amplitude, and (E) on a basis of the first and second data for defect amount estimation and the first and second amplitude, estimating a defect cross-sectional area and a defect width of the defect part.

2. The testing method using a guided wave according to claim 1, wherein the first data for defect amount estimation is represented by a following function F:

$$F(y,z)=x,$$

where x is a dependent variable and y, z are independent variables, and x denotes amplitude of the reflected wave, y denotes a defect cross-sectional area and z denotes a defect width, the second data for defect amount estimation is represented by a following function G:

$$G(y,z)=x,$$

where y, z are independent variables and x is a dependent variable, and x denotes amplitude of the reflected wave, y denotes a defect cross-sectional area and z denotes a defect width, and in (E), $F(y, z)=x_f$ and $G(y, z)=x_g$ are solved as a set of simultaneous equations, where $x_f$ denotes the first amplitude for the function F and $x_g$ denotes the second amplitude for the function G, whereby the defect cross-sectional area and the defect width of the defect part are calculated.

3. The testing method using a guided wave according to claim 1, wherein in (A) or (B), (a) a subject for testing of a same type as the subject as a testing target is prepared;

(b) a guided wave of the first or second frequency is propagated through the subject for testing and amplitude of a reflected wave thereof at a defect part is detected;

(c) (b) is performed for a plurality of defect parts and, (d) on a basis of a defect cross-sectional area and a defect width of each of the plurality of defect parts in (c) and a plurality of the amplitude values obtained in (c), the first or second data for defect amount estimation is obtained.

4. The testing method using a guided wave according to claim 2, wherein in (A) or (B), (a) a subject for testing of a same type as the subject as a testing target is prepared;

(b) a guided wave of the first or second frequency is propagated through the subject for testing and amplitude of a reflected wave thereof at a defect part is detected;

(c) (b) is performed for a plurality of defect parts and, (d) on a basis of a defect cross-sectional area and a defect width of each of the plurality of defect parts in (c) and a plurality of the amplitude values obtained in (c), the first or second data for defect amount estimation is obtained.

* * * * *